(12) United States Patent
Suga et al.

(10) Patent No.: US 9,498,310 B2
(45) Date of Patent: Nov. 22, 2016

(54) FULL DENTURE BASE MANUFACTURING METHOD

(71) Applicant: GC Corporation, Tokyo (JP)

(72) Inventors: Takeo Suga, Kanagawa (JP); Masataka Itoda, Osaka (JP); Hideaki Yasaki, Tokyo (JP); Yasuhiro Yokoyama, Chiba (JP); Shuichi Nomura, Niigata (JP); Hiroshi Kamohara, Tokyo (JP)

(73) Assignee: GC Corporation, Tokyo (JP)

( * ) Notice: Subject to any disclaimer, the term of this patent is extended or adjusted under 35 U.S.C. 154(b) by 198 days.

(21) Appl. No.: 14/407,543

(22) PCT Filed: Jun. 17, 2013

(86) PCT No.: PCT/JP2013/066573
§ 371 (c)(1),
(2) Date: Dec. 12, 2014

(87) PCT Pub. No.: WO2013/191127
PCT Pub. Date: Dec. 27, 2013

(65) Prior Publication Data
US 2015/0190216 A1    Jul. 9, 2015

(30) Foreign Application Priority Data

Jun. 22, 2012 (JP) ................................. 2012-141191
Jul. 20, 2012 (JP) ................................. 2012-161864

(51) Int. Cl.
*A61C 9/00* (2006.01)
*A61C 13/01* (2006.01)
*A61C 13/34* (2006.01)

(52) U.S. Cl.
CPC .............. *A61C 13/01* (2013.01); *A61C 9/0006* (2013.01); *A61C 13/04* (2013.01); *A61C 13/34* (2013.01); *F04C 2270/041* (2013.01)

(58) Field of Classification Search
CPC ............................................ A61C 9/00–9/0093
USPC ............................................. 433/34–48, 213
See application file for complete search history.

(56) References Cited

U.S. PATENT DOCUMENTS 2,708,789 A * 5/1955 Opotow .................. A61C 13/00
433/71

4,235,594 A * 11/1980 Schwartz ............... A61C 19/05
433/213

(Continued)

FOREIGN PATENT DOCUMENTS

EP          1844729      10/2007
JP       H07-023984       1/1995

(Continued)

OTHER PUBLICATIONS

International Search Report mailed on Aug. 20, 2013.

*Primary Examiner* — Yogesh Patel
(74) *Attorney, Agent, or Firm* — IPUSA, PLLC (57) ABSTRACT

A full denture base manufacturing method is provided that can easily manufacture a full denture base, using a set of maxillary impression tray and a mandibular impression tray for taking an impression from a patient including an edentulous patient.

An impression material is applied on each of a maxillary impression tray 3 and a mandibular impression tray 4 configuring a set of impression trays, and respectively having a U-shaped groove, the U-shaped groove having a front surface side on which the impression material is to be applied and being provided with projecting parts 1 on a back surface side thereof, and the applied impression material is pressed against an alveolar ridge within an oral cavity and set, to determine bite position and height in a state in which at least a part of flat top surfaces of the projecting parts 1 contact each other, the second impression material is applied between back surfaces of the impression trays 3, 4 and set in a state in which at least a part of the flat top surfaces contact each other, each of the impression trays 3, 4 and the impression material are removed from within the oral cavity in one piece of the maxillary and mandibular impression trays, or separately in two pieces of the maxillary and mandibular impression trays, and a model material is thereafter injected to each impression material on the removed maxillary and mandibular impression trays and set, in order to manufacture an edentulous jaw model, and the edentulous jaw model is set on an articulator in a state in which the bite position and height that are determined in advance are reflected, in order to manufacture a full denture base.

1 Claim, 5 Drawing Sheets

(56) References Cited

U.S. PATENT DOCUMENTS

| | | | |
|---|---|---|---|
| 5,961,325 A | 10/1999 | Van Handel | |
| 6,152,730 A * | 11/2000 | Wildman | A61C 19/05 433/215 |
| 6,315,555 B1 * | 11/2001 | Bortolotti | A61C 9/0006 433/37 |
| 2009/0246729 A1 * | 10/2009 | Massad | A61C 19/05 433/71 |
| 2010/0269836 A1 * | 10/2010 | Roettger | A61O 5/14 128/861 |

FOREIGN PATENT DOCUMENTS

| | | |
|---|---|---|
| JP | H08-266561 | 10/1996 |
| JP | 2001-333917 | 12/2001 |
| JP | 2002-522151 | 7/2002 |
| WO | 00/09032 | 2/2000 |

* cited by examiner

FULL DENTURE BASE MANUFACTURING METHOD

TECHNICAL FIELD

The present invention relates to a full denture base manufacturing method that can easily manufacture a full denture base, using a set of a maxillary impression tray and a mandibular impression tray.

BACKGROUND ART

Generally, in odontotherapy, when taking an intraoral impression in a preparation stage of manufacturing prostheses, an impression material such as silicone impression materials, alginate impression materials, and the like is used. An impression tray is used to intraorally hold such an impression material. The impression material is applied on the impression tray that is inserted into an oral cavity of a patient, and after the impression material is pressed for taking an impression and is set, the impression tray is removed from the oral cavity of the patient in a state in which the set impression material is integrally held on the impression tray.

When taking such an impression from an edentulous patient (including a substantially edentulous patient), the impression must be taken from an alveolar ridge that forms a smooth curve. In this case, an extremely high accuracy is required, such as when pressing the impression material against the alveolar ridge with a uniform force.

For this reason, in order to more accurately take the intraoral impression, the impression is in many cases taken twice from the edentulous patient.

More particularly, a first impression is taken from the alveolar ridge by first using a general impression tray, and an edentulous jaw model is thereafter manufactured from the set impression material. Then, an impression tray (hereinafter referred to as a personal tray) exclusively for the edentulous patient is manufactured from the edentulous jaw model.

Next, the impression material is thinly applied on the personal tray, and a second impression is taken from the alveolar ridge, in order to manufacture a more accurate edentulous jaw model from the impression.

In the case of an edentulous patient, bite position and height must be determined separately because the edentulous patient has no teeth. Hence, a large number of processes, including measurements made from outside the face using a measuring apparatus and the like, determining the bite position and height by reflecting measured data to the edentulous jaw model on an articulator, and the like, are carried out in order to finally manufacture a full denture base.

As the impression tray for use in taking the impression from the edentulous patient, there is an impression tray for maxillary mucosa of the edentulous patient, applied with an utility wax, and including a peripheral wall part having an edge that makes contact with each mucosa at a bottom of a valley-shaped part between a cheek and a maxillary alveolar ridge of the patient having the edentulous alveolar ridge, and at an inner part of an maxillopalatine lower surface, a bottom plate part connected to a large portion of an edge on an opposite side from the edge of the peripheral wall part and provided with an impression material injection opening only at a part near the alveolar ridge at a front part of the peripheral wall part, and a handle provided on the front part of the peripheral wall part (refer to Patent Document 1, for example).

This impression tray for maxillary mucosa is for use in supplying and setting a slurry of a plaster impression material in order to take an accurate impression in a non-pressure state, and is applied with the utility wax so that the slurry of the impression material does not drop or leak from the impression tray (refer to paragraphs 0002-0005 of specification of Patent Document 1), and the impression only needs to be taken once.

However, this impression tray is merely for taking the impression of the alveolar ridge (refer to paragraph 0001 of specification of Patent Document 1), and no data can be obtained with respect to the bite position and height. For this reason, the full denture base cannot be manufactured by simply taking the impression using this impression tray, and as in the conventional case, the bite position and height must be determined through separate measurements and the like.

PRIOR ART DOCUMENTS

Patent Documents

Patent Document 1: Japanese Laid-Open Patent Publication No. H07-23984 (1995-023984)

DISCLOSURE OF THE INVENTION

Problem to be Solved by the Invention

One object of the present invention is to provide a full denture base manufacturing method that can easily manufacture a full denture base, using a set of a maxillary impression tray and a mandibular impression tray for use in taking an impression of a patient including an edentulous patient.

Means of Solving the Problem

As a result of diligent research conducted to solve the problem described above, the present inventors found that when an impression material is applied on each of a maxillary impression tray and a mandibular impression tray configuring a set of impression trays and respectively having a U-shaped groove, the U-shaped groove having a front surface side on which the impression material is to be applied and being provided with projecting parts on a back surface side thereof, the applied impression material is pressed against an alveolar ridge within an oral cavity and set, and bite position and height are determined in a state in which at least a part of flat top surfaces of the projecting parts contact each other, the bite position and height can easily be determined simultaneously as when the impression is taken. In addition, the present inventors found that when a second impression material is applied between back surfaces of the impression trays and set in a state in which at least a part of the flat top surfaces contact each other, data related to the bite position and height can easily be copied and transferred to the impression material. Furthermore, the present inventors found that when each of the impression trays and the impression material are removed from within the oral cavity in one piece of the maxillary and mandibular impression trays, or separately in two pieces of the maxillary and mandibular impression trays, and a model material is thereafter injected to each impression material on the removed maxillary and mandibular impression trays and set in order to manufacture an edentulous jaw model, and the edentulous jaw model is set on an articulator in a state in which the bite position and height that are determined in advance are reflected in order to manufacture a full denture base, processes that need to be carried out separately, such as determining the bite position and height, can be omitted, and the full denture base can be manufactured quickly and with ease. The present inventors completed the present invention based on these findings.

In other words, a full denture base manufacturing method according to the present invention is characterized by applying an impression material on each of a maxillary impression tray and a mandibular impression tray configuring a set of impression trays, and respectively having a U-shaped groove, the U-shaped groove having a front surface side on which the impression material is to be applied and being provided with projecting parts on a back surface side thereof; pressing the impression material against an alveolar ridge within an oral cavity and setting the impression material, and determining bite position and height in a state in which at least a part of flat top surfaces of the projecting parts contact each other; applying a second impression material between back surfaces of the impression trays in a state in which at least a part of the flat top surfaces contact each other; setting the second impression material; removing each of the impression trays and the impression material from within the oral cavity in one piece of the maxillary and mandibular impression trays, or separately in two pieces of the maxillary and mandibular impression trays, and thereafter injecting a model material to each impression material on the removed maxillary and mandibular impression trays and setting the model material in order to manufacture an edentulous jaw model; and setting the edentulous jaw model on an articulator in a state in which the bite position and height that are determined in advance are reflected in order to manufacture a full denture base.

Effects of the Invention

The full denture base manufacturing method according to the present invention applies an impression material on each of a maxillary impression tray and a mandibular impression tray configuring a set of impression trays and respectively having a U-shaped groove, the U-shaped groove having a front surface side on which the impression material is to be applied and being provided with projecting parts on a back surface side thereof, presses the applied impression material against an alveolar ridge within an oral cavity and sets the impression material, and determines bite position and height in a state in which at least a part of flat top surfaces of the projecting parts contact each other. Hence, the bite position and height can easily be determined simultaneously as when the impression is taken. In addition, the present invention applies a second impression material between back surfaces of the impression trays and sets the second impression material in a state in which at least a part of the flat top surfaces contact each other. Thus, data related to the bite position and height can easily be copied and transferred to the impression material. Furthermore, the present invention removes each of the impression trays and the impression material from within the oral cavity in one piece of the maxillary and mandibular impression trays, or separately in two pieces of the maxillary and mandibular impression trays, and thereafter injects a model material to each impression material on the removed maxillary and mandibular impression trays and sets the model material in order to manufacture an edentulous jaw model, and sets the edentulous jaw model on an articulator in a state in which the bite position and height that are determined in advance are reflected in order to manufacture a full denture base. For this reason, processes that need to be carried out separately, such as determining the bite position and height, can be omitted, and the full denture base can be manufactured quickly and with ease.

MODE OF CARRYING OUT THE INVENTION

A detailed description will hereinafter be given of the full denture base manufacturing method according to the present invention, by referring to the drawings. In the drawings, An U-shaped groove 2 has a front surface side on which an impression material is to be applied and provided with projecting parts 1 on a back surface side thereof. In addition, the projecting part 1 has a flat top surface 1a, as illustrated in FIGS. 1 and 3-5.

When the projecting parts 1 are provided on the back surface of each of a maxillary impression tray 3 and a mandibular impression tray 4 which will be described later, at the U-shaped groove 2 for positioning each of left and right alveolar ridges from a first molar part to a premolar part, a pair of projecting parts 1 is arranged on the left and right at approximately an intermediate part between the front teeth and the molars. Hence, by adjusting positions in a state in which at least a part of the flat top surfaces 1a of the projecting parts 1 contact each other, positions of the maxillary impression tray 3 and the mandibular impression tray 4 can be determined at various bite positions and heights.

Each of the maxillary impression tray 3 and the mandibular impression tray 4 is provided with the projecting parts 1 and the U-shaped groove 2 described above. As illustrated in FIGS. 1-8, each of these impression trays is preferably provided with elongated holes 5 and the like through which the impression material is pushed out and combined into one piece. In addition, as illustrated in FIGS. 1-6, the mandibular impression tray 4 needs to have a shape that does not have a part corresponding to a tongue part.

Figure 3:
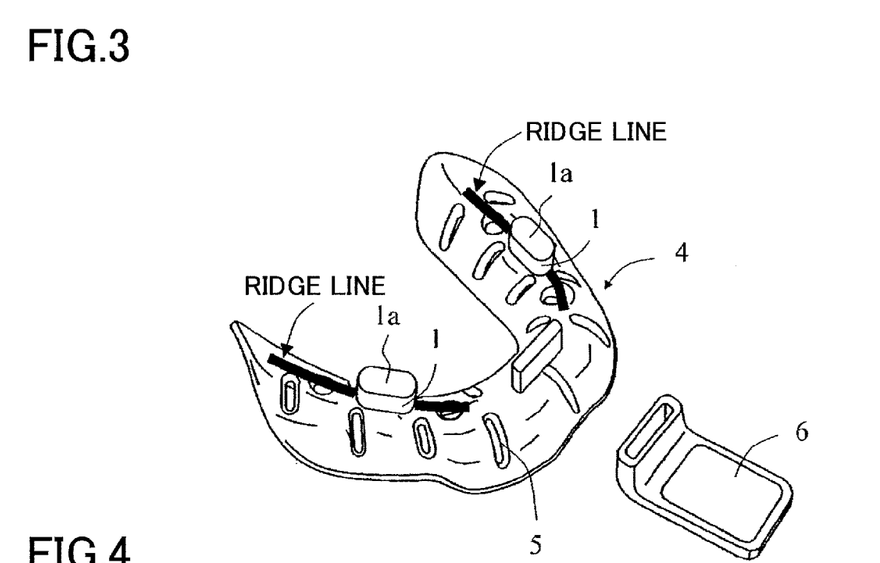
FIG. 3 is a perspective view illustrating a mandibular impression tray illustrated in FIG. 1 in a state in which a handle part is removed.
Figure 4:
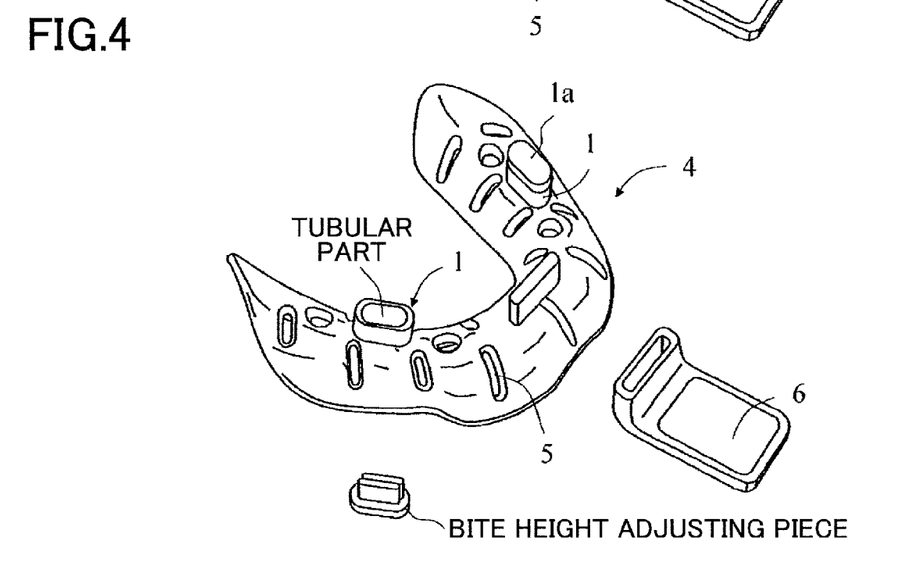
FIG. 4 is a perspective view illustrating another embodiment of the mandibular impression tray used in the full denture base manufacturing method according to the present invention.
Figure 5:
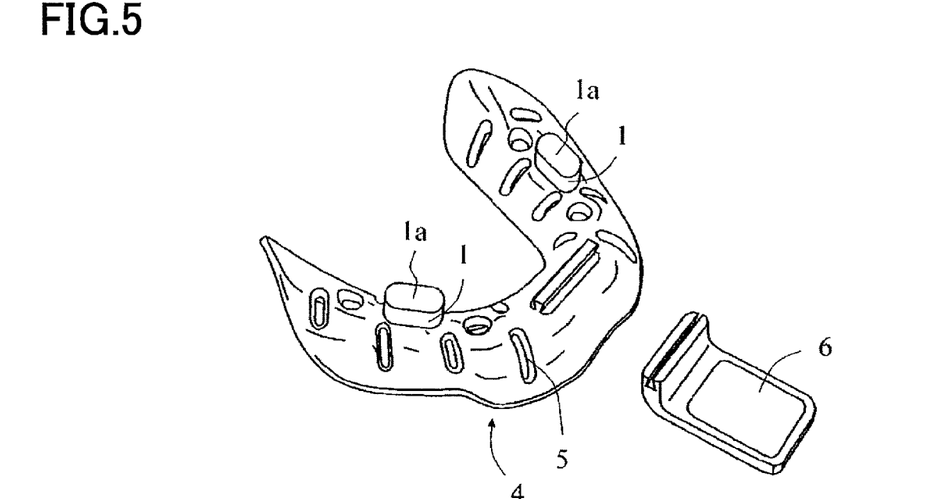
FIG. 5 is a perspective view illustrating still another embodiment of the mandibular impression tray used in the full denture base manufacturing method according to the present invention.

Further, when a handle part 6 of each of the impression trays 3 and 4 is made to be detachable as illustrated in FIGS. 3-5, the handle part 6 may be removed when taking the impression, and it is possible to prevent an inaccurate impression caused by the handle part 6 hitting a lip.

Next, a detailed description will be given of the full denture base manufacturing method according to the present invention, which uses the set of the maxillary impression tray 3 and the mandibular impression tray 4.

First, when using each of the impression trays 3 and 4 to take the impression, the impression may be taken carefully once, or the impression may be taken twice for more accuracy. Even in the case in which the impression is taken twice, it is not a precondition in the full denture base manufacturing method according to the present invention to manufacture a personal tray other than each of the impression trays 3 and 4. Hence, after the first impression is taken by the the maxillary impression tray 3 and the mandibular impression tray 4, a new impression material is thinly applied on the top surface of the impression material on the impression trays 3 and 4 in order to take the second impression.

Figure 6:
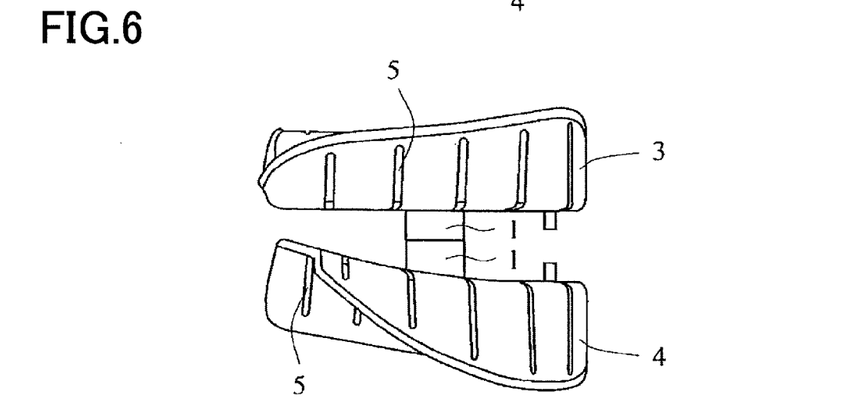
FIG. 6 is an explanatory side view illustrating a state in which the handle parts are removed from the set of impression trays illustrated in FIG. 1 and top surfaces of projecting parts of the impression trays make contact in a state in which the top surfaces are parallel.
Figure 7:
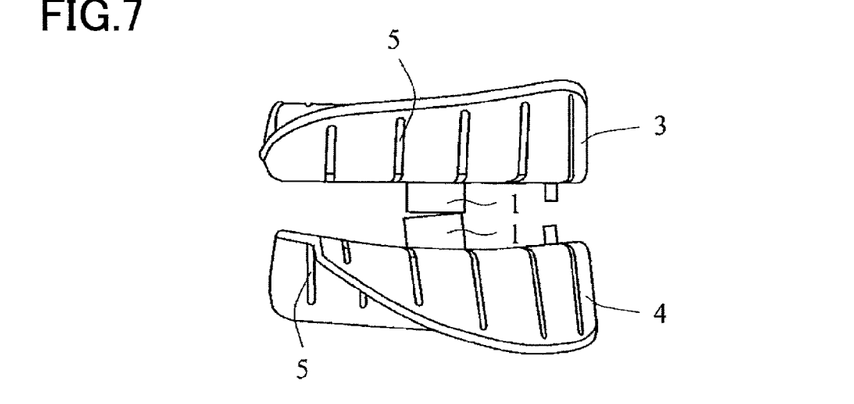
FIG. 7 is an explanatory side view illustrating a state in which the handle parts are removed from the set of impression trays illustrated in FIG. 1 and the top surfaces of the projecting parts of the impression trays make partial contact in a state in which the top surfaces are inclined.
Figure 8:
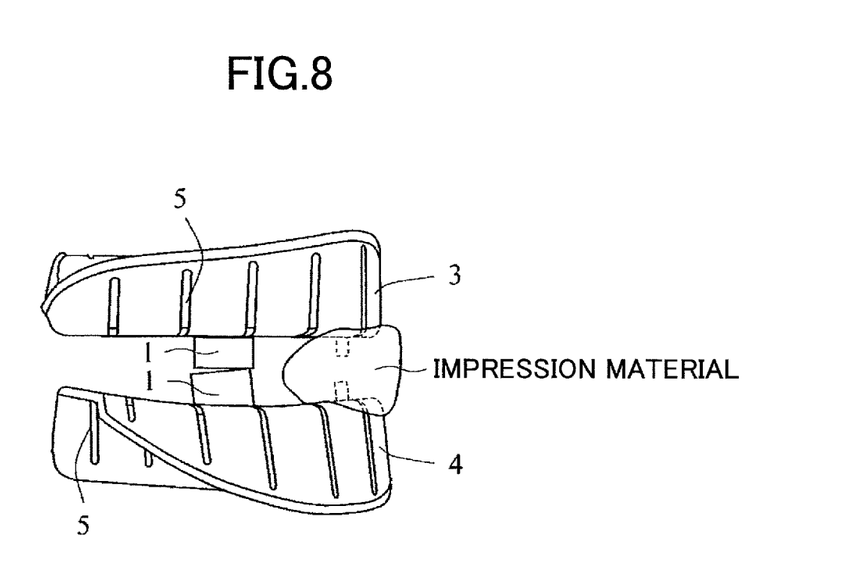
FIG. 8 is an explanatory side view illustrating a state in which an impression material is applied between back surfaces of the set of impression trays illustrated in FIG. 7 and set.

As illustrated in FIGS. 6-8 (explanatory side views in which the impression material provided on the surface is omitted), when the maxillary impression tray 3 and the mandibular impression tray 4 are used in a state in which the handle parts 6 are removed, it is possible to prevent the inaccurate impression caused by the handle parts 6 hitting the lip. In this case, when pressing the impression material against the alveolar ridge within an oral cavity, the projecting parts 1 of each of the maxillary impression tray 3 and the mandibular impression tray 4 are pushed by fingers, and the impression material can easily be pressed against the alveolar ridge without causing the excess impression material to stick to a hand.

When taking the impression in this manner, the patient is urged to bite while gradually moving the maxillary impression tray 3 and the mandibular impression tray 4 within the oral cavity, in order to look for an appropriate bite position and height at the position where the top surfaces 1a of the projecting parts 1 of the maxillary impression tray 3 and the mandibular impression tray 4 make contact with each other.

In this case, the bite position and height may be determined after the impression material applied on the maxillary impression tray 3 and the mandibular impression tray 4 sufficiently set, or the bite position and height may be determined in a state in which the impression material is not yet completely set.

When the projecting part 1 is formed so that a longitudinal direction thereof matches a ridge line direction at the back surface of the U-shaped groove 2 as illustrated in FIG. 3, and a length thereof in the longitudinal direction is 5 mm to 20 mm and a width in a width direction is 3 mm to 10 mm, it is possible to prevent a state in which the maxillary and mandibular projecting parts do not make contact due to the patient's jaw position. Furthermore, when relatively small projecting parts are used, it is preferable in that the projecting parts can easily be moved even to the bite position and height where the projecting parts are inclined and held at the inclined position. When the length of the projecting part 1 in the longitudinal direction thereof is less than 5 mm, the projecting part 1 is too short, and it may not be easy to make at least a part of the flat top surfaces 1a of the projecting parts 1 of the maxillary impression tray 3 and the mandibular impression tray 4 contact each other when determining the bite position and height. On the other hand, when the length of the projecting part 1 in the longitudinal direction thereof exceeds 20 mm, the projecting part 1 is too long, and it becomes not easy to tilt the top surface or maintain the position of the projecting part. Moreover, when the width of the projecting part 1 in the width direction thereof is less than 3 mm, the projecting part 1 is too narrow, and it may not be easy to make at least a part of the flat top surfaces 1a of the projecting parts 1 of the maxillary impression tray 3 and the mandibular impression tray 4 contact each other when determining the bite position and height. On the other hand, when the width of the projecting part 1 in the width direction thereof exceeds 10 mm, the projecting part 1 is too wide, and an inconvenience such as the projecting part 1 hitting the cheek may occur.

Figure 1:
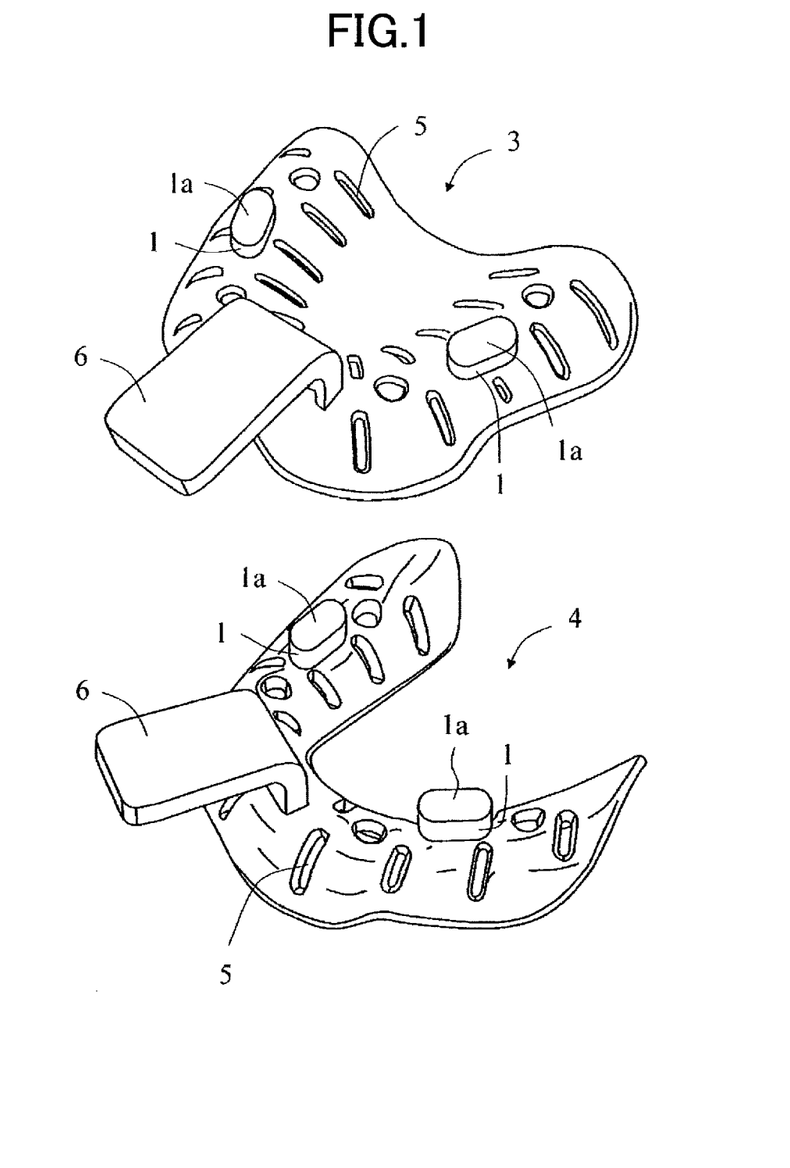
FIG. 1 is a perspective view illustrating one embodiment of a set of impression trays used in a full denture base manufacturing method according to the present invention, in a state viewed from a back surface side.
Figure 2:
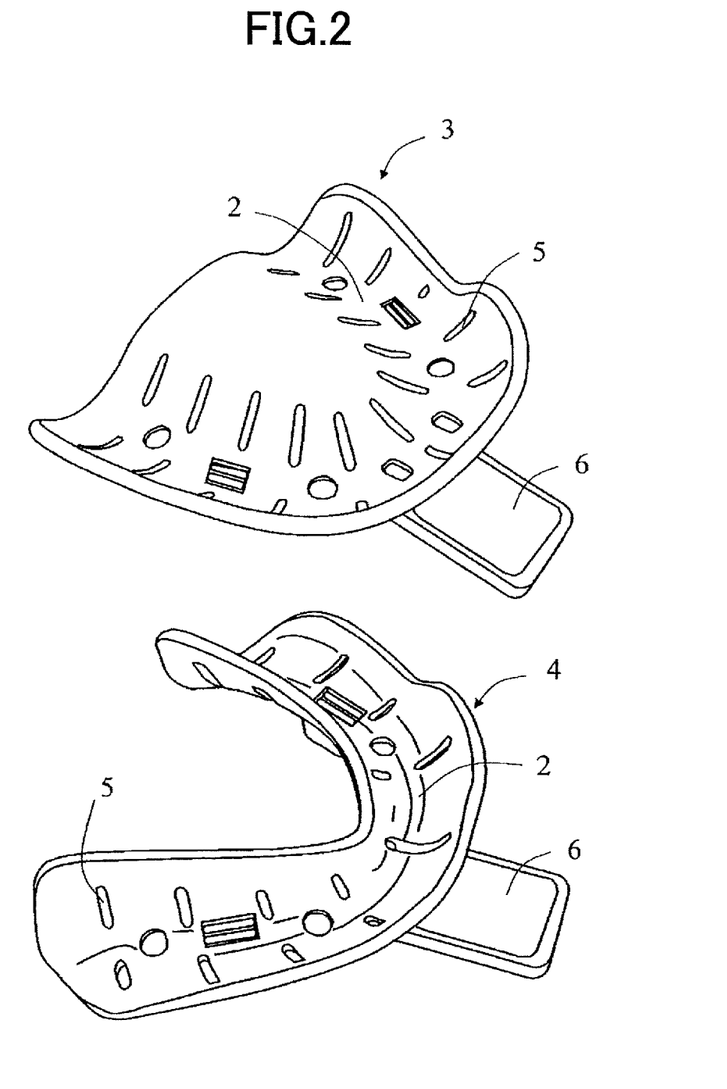
FIG. 2 is a perspective view illustrating the set of impression trays illustrated in FIG. 1 viewed from a front surface side.

The projecting parts 1 may be integrally formed on the maxillary impression tray 3 and the mandibular impression tray 4 in advance, as illustrated in FIGS. 1, 3, and 5, or may be formed by a self-setting resin before using each of the impression trays 3 and 4. When the projecting part 1 is formed by a tubular part and a bite height adjusting piece, as illustrated in FIG. 4, the height of the projecting part 1 can be changed with ease, and it is preferable in that an accurate bite position and height can easily be determined.

After the bite position and height are determined in the above described manner, a second impression material is applied between the back surfaces of the maxillary impression tray 3 and the mandibular impression tray 4 and set (FIG. 8). The positions of the maxillary impression tray 3, the mandibular impression tray 4, and the impression material applied therebetween are fixed in a state in which the determined bite position and height are reflected.

The second impression material to be applied between the back surfaces of the impression trays 3 and 4 may be applied on the front teeth side as illustrated in FIG. 8, or between the projecting parts 1 whose top surfaces 1a make contact, although not illustrated in the drawings.

The impression trays 3 and 4 and the impression material, whose positions are fixed, are removed from within the oral cavity in one piece of the maxillary and mandibular impression trays, or separately in two pieces of the maxillary and mandibular impression trays. In a case in which the maxillary and mandibular impression trays in one piece is too large, for example, and the removal in one piece from the oral cavity is difficult, the set second impression material provided between the back surfaces of the impression trays 3 and 4 may be left on one of the impression trays 3 and 4 when removing them separately, and the bite position and height can easily be reproduced by combining the two impression trays 3 and 4 after their removal.

Next, a model material is injected to each impression material on the removed maxillary and mandibular impression trays and set, in order to manufacture an edentulous jaw model. This edentulous jaw model is set on an articulator in a state in which the bite position and height that are determined in advance are reflected, and the full denture base can thereafter be manufactured according to a known method. Hence, processes conventionally carried out to determine the bite position and height can be omitted, and the full denture base can be manufactured quickly and with ease.

DESCRIPTION OF REFERENCE NUMERALS

1 Projecting Part
1a Top Surface
2 U-shaped Groove
3 Maxillary Impression Tray
4 Mandibular Impression Tray
5 Elongated Hole
6 Handle Part

The invention claimed is:

1. A full denture base manufacturing method comprising:

applying an impression material on each of a maxillary impression tray and a mandibular impression tray configuring a set of impression trays and respectively having a U-shaped groove, the U-shaped groove having a front surface side on which the impression material is to be applied and being provided with projecting parts on a back surface side thereof;

pressing the impression material against an alveolar ridge within an oral cavity and setting the impression material, determining bite position and height in a state in which at least a part of flat top surfaces of the projecting parts contact each other;

applying a second impression material between back surfaces of the impression trays in a state in which at least a part of the flat top surfaces contact each other;

setting the second impression material;

removing each of the impression trays and the impression material from within the oral cavity in one piece of the maxillary and mandibular impression trays, or separately in two pieces of the maxillary and mandibular impression trays, thereafter injecting a model material to each impression material on the removed maxillary and mandibular impression trays and setting the model material in order to manufacture an edentulous jaw model;

and setting the edentulous jaw model on an articulator in a state in which the bite position and height that are determined in advance are reflected in order to manufacture a full denture base.

* * * * *